(12) United States Patent
Borden

(10) Patent No.: US 8,394,419 B2
(45) Date of Patent: *Mar. 12, 2013

(54) BONE GRAFT MATERIALS DERIVED FROM MINERALIZED GELATIN

(75) Inventor: Mark Borden, Collegeville, PA (US)

(73) Assignee: Global Medical, Inc., Audubon, PA (US)

( * ) Notice: Subject to any disclaimer, the term of this patent is extended or adjusted under 35 U.S.C. 154(b) by 1 day.

This patent is subject to a terminal disclaimer.

(21) Appl. No.: 12/985,515

(22) Filed: Jan. 6, 2011

(65) Prior Publication Data

US 2011/0104299 A1    May 5, 2011

Related U.S. Application Data

(60) Division of application No. 11/423,839, filed on Jun. 13, 2006, now Pat. No. 7,892,577, which is a continuation of application No. 11/362,540, filed on Feb. 27, 2006, now Pat. No. 7,785,634.

(51) Int. Cl.
*A61F 2/00* (2006.01)
*A61F 2/28* (2006.01)
*A61K 35/32* (2006.01)

(52) U.S. Cl. ........ 424/549; 424/422; 424/423; 424/499; 623/16.11

(58) Field of Classification Search .............. 424/422, 424/423, 499, 549; 623/16.11
See application file for complete search history.

(56) References Cited

U.S. PATENT DOCUMENTS

| | | | |
|---|---|---|---|
| 2,028,935 A | 1/1936 | Knoll |
| 3,892,876 A | 7/1975 | Hobday |
| 5,073,373 A | 12/1991 | O'Leary |
| 5,356,630 A | 10/1994 | Laurencin |
| 5,455,231 A | 10/1995 | Constantz |
| 5,585,116 A | 12/1996 | Boniface |
| 6,165,515 A | 12/2000 | Matsuyama |
| 6,309,659 B1 | 10/2001 | Clokie |
| 6,575,249 B2 | 6/2003 | Deaton |
| 6,623,748 B2 | 9/2003 | Clokie |
| 6,652,887 B1 | 11/2003 | Richelsoph |
| 7,132,110 B2 | 11/2006 | Kay |
| 2002/0098222 A1 | 7/2002 | Wironen |
| 2003/0044445 A1 | 3/2003 | Kay |
| 2004/0097612 A1 | 5/2004 | Rosenberg |
| 2005/0203206 A1 | 9/2005 | Trieu |
| 2005/0267577 A1 | 12/2005 | Trieu |
| 2007/0202191 A1 | 8/2007 | Borden |

FOREIGN PATENT DOCUMENTS

CN    1328774 A   *   1/2002

OTHER PUBLICATIONS

Albritton, 2005, "Brothy Benefits. An Age-old Tradition Making a Comeback", www.chesapeakegardens.com/articles/brothy.benefits.pdf. p. 1-3.
Fallon 2000, "Broth is Beautiful" from www.westonaprice.org/foodfeatures/broth.html. p. 1-9.
"Health Benefits of Bone Broth", 2009. http://wss.nourishingconnections.org/Education/Broth%20Benefits.doc. p. 1-2.
International Preliminary Report on Patentability in related PCT application PCT/US07/62833, dated Sep. 12, 2008.
International Search Report and Written Opinion in related PCT application PCT/US07/62833, dated May 7, 2008.

* cited by examiner

*Primary Examiner* — Taeyoon Kim

(57) ABSTRACT

The present invention provides novel methods of forming mineralized gelatin carriers from bone. The present invention further provides mineralized gelatin carriers themselves; bone products that include such mineralized gelatin carriers including DBM bone products; and kits that include mineralized gelatin carriers formed from bone. The present invention further provides methods for making DBM bone products, wherein both the DBM and a mineralized gelatin carrier for the DBM are derived independently from a bone lot.

5 Claims, 3 Drawing Sheets

BONE GRAFT MATERIALS DERIVED FROM MINERALIZED GELATIN

RELATED APPLICATIONS

This application is a Divisional of U.S. Application Ser. No. 11/423,839 filed on Jun. 13, 2006, now U.S. Pat. No. 7,892,577 which is a Continuation of U.S. application Ser. No. 11/362,540 filed on Feb. 27, 2006, now U.S. Pat. No. 7,785,634, the contents of each of which are hereby incorporated herein by reference in their entireties.

FIELD OF THE INVENTION

The present invention provides novel methods of forming mineralized gelatin carriers from bone, such as cortical or cancellous bone. The present invention also provides mineralized gelatin carriers themselves; bone products that include such mineralized gelatin carriers including DBM bone products; and kits that include mineralized gelatin carriers formed from bone. The present invention further provides methods for making bone products, wherein both the bone graft products and a mineralized gelatin carrier are derived independently from a bone lot. Also provided are surgical implants and devices that include mineralized carriers or bone products thereon or incorporated therewith. The present invention further provides methods of treatment using mineralized carriers, bone products, or surgical implants or devices of the present invention.

BACKGROUND OF THE INVENTION

Bone grafting is a common procedure performed by orthopedic trauma and spinal surgeons to regenerate tissue at a site affected by trauma, disease, or deformity. Graft materials include bone taken from the patient's own skeleton, allograft bone derived from tissue donors, and synthetics that consist of porous ceramics and polymers. Demineralized bone matrix (DBM), is a special type of bone graft that actively stimulates bone formation due to the presence of growth factors within the DBM particles. Derived from allogeneic cortical bone, DBM has been widely used in a variety of orthopedic cases. However, the particulate nature of DBM has made its delivery and containment difficult.

To improve the handling properties of DBM, several companies have developed products that combine DBM particles with a gel-like carrier to try to improve the handling and graft containment of DBM at the surgical site. However, not all carriers perform equally well as a DBM delivery vehicle. For example, the combination of glycerol and DBM, disclosed in U.S. Pat. No. 5,073,373, results in a moldable putty, however, the glycerol component is highly soluble in water and body fluids, and can readily wash away from the graft site. The combination of a thermally reversible copolymer and DBM, disclosed in U.S. Pat. No. 6,309,659, improves upon the solubility of the carrier, however, studies have shown that the final product has variable biological activity [Wang J C, et al "Prospective comparison of commercially available demineralized bone matrix for spinal fusion". Trans. North Am. Spine Soc 2000; 15:35-37]. Another DBM product, disclosed in U.S. Pat. No. 6,652,887, is a combination of calcium sulfate, carboxymethylcellulose, water, and DBM. Although this product handles well and is resistant to irrigation, the DBM is enclosed in a carrier that disadvantageously takes 6 to 8 weeks to resorb. With typical graft incorporation occurring within the first 72 hours, the delayed resorption of the carrier can interfere with the healing response. [Lee Y P, Wang J C, Kanim L E, Jo M J, Davis M, Lieberman J R. "The direct comparison of different commercially available demineralized bone matrix substances in an athymic rat model." Trans North Am Spine Soc 2001; 16:86-87].

The use of bone in gelatin manufacturing has been a widely used process since the early 1900s. By weight, bone is approximately 70% mineral, 20% collagen, 5% growth factors, and 5% water [Bostrom, M P, Boskey A, Kaufman J K, Einhorn T A. "Form and Function of Bone." *Orthopaedic Basic Science*. Buckwalter J A, Einhorn T A, Simon S R. (eds). Rosemont: American Academy of Orthopaedic Surgeons. pp. 327-328 (2000)]. Through various processing methods, the cross-linked collagen component of bone can be broken down to create gelatin. The gelatin molecule consists of collagen fragments that interact together to form rigid and semi rigid gels at room temperature and below. Standard gelatin manufacturing processes using bone as a raw material, start by treating the bone with an acidic solution to dissolve the bone mineral. The remaining material called ossein is composed of 80% collagen by dry weight. A combination of acids, bases, and high temperature can be used to break apart the collagen molecules in ossein to create gelatin fragments. Done in several extraction steps, a range of purified gelatin solutions can be obtained. Similar processing has been disclosed to create gelatin from human bone to be used as a carrier for DBM. All of these techniques use DBM as a starting material. Although DBM and ossein are chemically similar, DBM processing is slightly different in that care must be taken to maintain biological activity of the growth factors found in bone.

In commercial gelatin production, more aggressive processes are used during demineralization because the goal is to eventually extract only purified gelatin. Gendler et al. followed standard gelatin processing and discloses a method for treating DBM with high temperatures and pressures to thermally degrade the collagen to create gelatin (U.S. Pat. No. 6,576,249). This was accomplished using autoclaves and other pressure vessels. Although the biological activity of the DBM is destroyed, active DBM is added back to the gelatin to create a DBM putty. Although human gelatin is formed using the Gendler process, the single step exposure of DBM to pressure and temperature produces gels of low quality with varying properties. The resulting DBM bone graft putties have poor handling and vary from lot to lot.

Kay et al. used a gentler approach to extracting gelatin by treating DBM with acids, bases, and/or salts to chemically degrade the collagen at room temperature and below (U.S. Published Patent Application 2003/0044445). In this process, the room temperature extraction can maintain some of the biological activity of the growth factor content of DBM. However, the low temperature extraction limits the amount and quality of gelatin produced from the extraction process. In both techniques, DBM is used as a starting material, and the resulting gel is composed of protein fragments from collagen and other proteins found in human DBM. Bone graft materials manufactured from these gels are formed by combining the DBM-derived gelatin with DBM particles.

SUMMARY OF THE INVENTION

The present invention provides novel techniques for creating a mineralized gelatin carrier from bone. In the present processes, bone (such as cortical bone or cancellous bone), not DBM, is used as the starting material. The use of mineralized bone allows for the resultant gelatin to contain the calcium and phosphate ions used during the bone regeneration process. Additionally, the process is conducted in a series of extraction steps which allow for the isolation of high quality human gelatin. Using a combination of acid, heat, and ultrasonic agitation, bone can be solubilized into a gelatin solution that contains bone mineral. These processes not only chemically and thermally degrade the collagen into gelatin fragments, but also dissolve the calcium phosphate bone mineral. Various processes may optionally be used to solubilize the bone into a gelatin solution containing bone mineral. For example, various combinations of heat, acids, sonication, bases, salts, and/or pressure may be used. Once neutralized, the gelatin solution contains both collagen fragments and soluble salts of calcium and phosphate. After the gelatin solution is cooled, this results in a mineralized gel that makes an effective carrier for particulate DBM. In addition to effectively delivering and maintaining the DBM graft at the surgical site, the mineralized gel also provides the bone regeneration site with a source of calcium and phosphate ions needed during remineralization.

In particular, the present invention provides methods of forming mineralized carriers from bone, and is further directed to mineralized carriers produced from such methods. The present invention further provides mineralized carriers that include calcium and phosphate, regardless of their method of production. By way of non-limiting example, the calcium and phosphate may be in the form of salts of calcium and phosphate.

The present invention also provides methods for producing bone products, which include one or more bone graft materials and one or more mineralized carriers. The bone graft materials include, but are not limited to, demineralized bone matrix (DBM), autograft bone, allograft cortical bone, allograft cancellous bone, synthetic bone grafts such as calcium phosphate and polymer bone graft substitutes, cellular materials such as marrow cells, osteoblasts, or mesenchymal stem cells, and/or growth factors such as BMP, TGF-B, VEGF, and FGF. The bone graft material and the mineralized carriers used to make such products may each be independently formed from bone, such as cortical bone. The present invention further provides bone products that include one or more bone graft materials and one or more mineralized carriers. Bone products in accordance with the present invention may be in the form of sheets, putties, pastes, sponges, gels, blocks and the like, and may be formed into any desired shape.

The present invention further provides kits, which include one or more mineralized carriers. The mineralized carriers included in such kits may be formed from bone in accordance with the methods of the present invention. Alternatively, the one or more carriers may be formed using other methods, which result in a mineralized carrier that includes calcium and phosphate, for example in the form of salts.

Kits in accordance with the present invention may further include one or more additional components, for example, a liquid for reconstituting mineralized carrier from a powder or other dried form; a container for combining the carrier with one or more other components; an apparatus (such as a form or mold) in which or on which to form a mineralized carrier into a specific shape; and/or DBM or other bone graft components to be combined with the carrier, for example such that the user can determine the ratio of DBM to carrier they wish to use.

The present invention also provides surgical implants or devices including mineralized carriers or bone graft products incorporated therewith or thereon. Further provided are methods of treatment, which include injecting or inserting a bone graft product, surgical implant or device in accordance with the present invention, into a patient in need thereof.

DETAILED DESCRIPTION OF THE INVENTION

Figure 1:
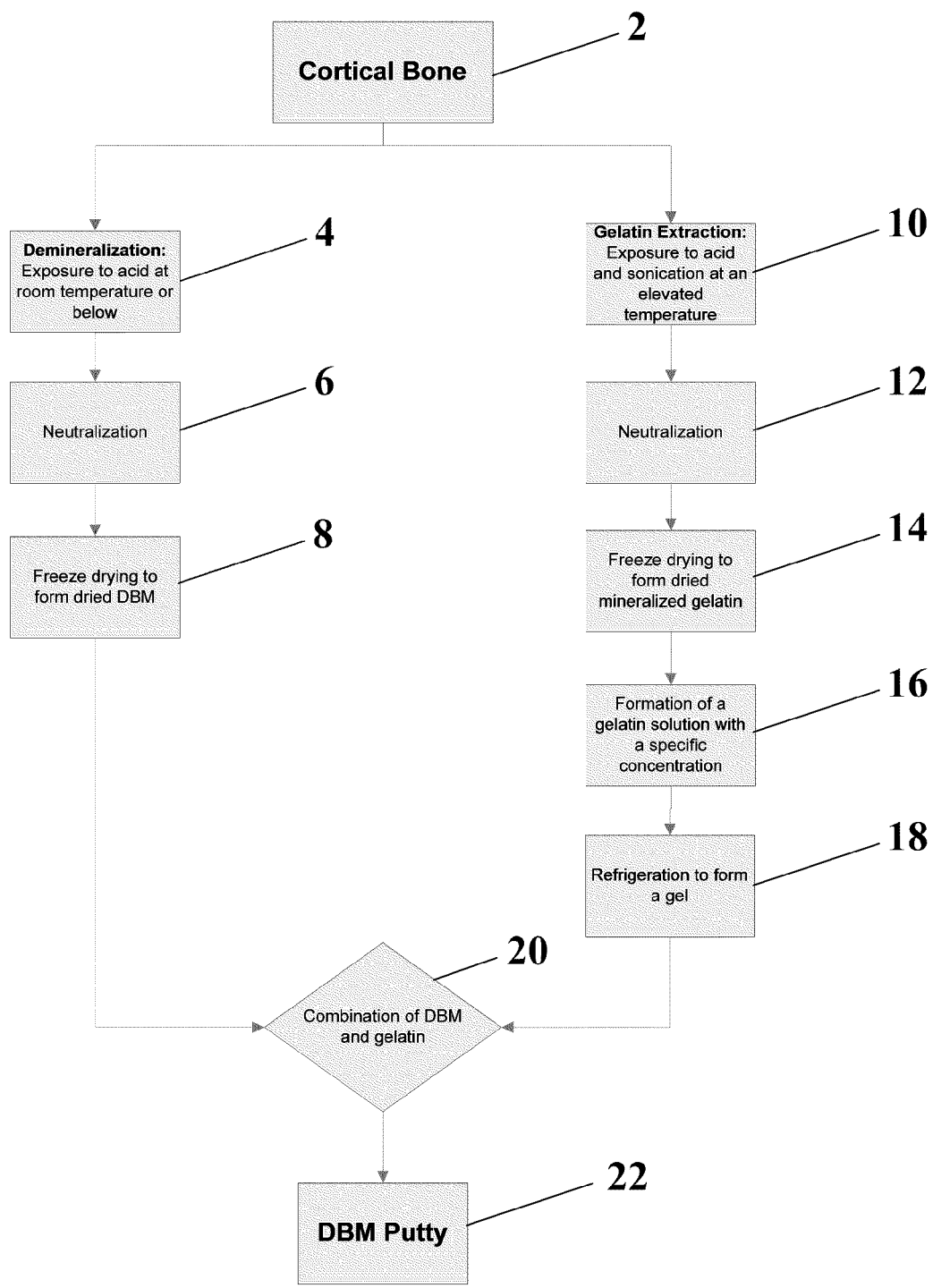
FIG. 1 is a flow chart of a general process for creating a mineralized DBM putty from a single lot of cortical bone, in accordance with certain embodiments of the present invention.

The aspects, advantages and other features of the invention will become apparent in view of the following detailed description, which discloses various non-limiting embodiments of the invention. In describing embodiments of the present invention, specific terminology is employed for the sake of clarity. However, the invention is not intended to be limited to this specific terminology. It is to be understood that each specific element includes all technical equivalents that operate in a similar manner to accomplish a similar purpose. Additionally, all of the citations herein are incorporated by reference in their entirety.

As used herein, "a" or "an" may mean one or more. As used herein, "another" may mean at least a second or more.

As used herein, the terms "gel" and "gelatin" are used as they are understood in the art, and are used somewhat interchangeably herein. The term "gel" generally refers to a semi-solid form of "gelatin," which is a derived protein formed from the collagen of animal tissues. The term "gelatin solution" refers to a liquid or semi-liquid that includes gelatin. However, the use of the terms gel and gelatin are not intended to exclude liquid forms, which may convert to a non-liquid form, for example upon cooling.

The terms "mineralized gelatin," "mineralized gelatin carrier," "carrier" and "mineralized carrier composition" are all intended to encompass a composition that includes a mineralized carrier in accordance with the present invention, whether it is a carrier formed by the present methods (or variant methods that are intended to be encompassed by the present methods), or a carrier that has similar mineral properties as the mineralized carrier formed by the present methods. As discussed further herein, such carriers or compositions, and bone products that include such carriers or compositions include, but are not limited to a mineralized carrier, and optionally one or more additional ingredients.

In developing a suitable carrier for a bone graft material, the carrier may advantageously be a biocompatible gel that can effectively deliver and maintain the material, such as DBM, at the graft site of a patient. The carrier should be readily absorbed by the site within the first few weeks and should not interfere with the biological activity of the material, such as the growth factor component of DBM. Additionally, the carrier may contain materials that can aid in the regeneration of bone.

The present invention includes methods for deriving a mineralized gelatin carrier from human bone and for creating bone grafts. Prior gels created from processes that use demineralized bone as the starting material for the carrier are missing the natural mineral component found in typical bone grafts such as autograft and allograft. Using cortical or cancellous bone in the present processes gives the present gelatin a mineral component. From a grafting standpoint, the local cells that create new tissue must remineralize to form mature bone. Therefore, it is advantageous to provide a source of bone mineral to the site to aid this remineralization process. Additionally, the present processes are advantageous over processes that do not use heat, because heat of the present processes aids in the solubilization of the gelatin. Therefore, the present processes result in better quality gelatins. Furthermore, the present process for creating gelatin can use two or more extraction steps which prevent continued degradation of the gelatin solution during extraction. By limiting exposure of the gelatin solution to heat and acidic conditions in certain embodiments, the degradation process can be controlled and better quality gelatins can be extracted. This in turn gives products of the present methods a more cohesive feel and better graft containment properties.

Accordingly, the present invention provides methods for making a DBM bone product, which include separating a bone lot into a first portion and a second portion; processing the first portion to create dried demineralized bone matrix; extracting a mineralized gelatin solution from the second portion; neutralizing the extracted mineralized gelatin solution; converting the mineralized gelatin solution to a freeze dried mineralized gelatin; combining the freeze dried gelatin with water to form a gelatin solution with a specific concentration, and combining the dried demineralized bone matrix with the mineralized gelatin to form a DBM bone product. The extraction process may include for example, one or more steps of exposing the second portion of the bone lot to one or more of elevated temperatures, acids, sonication, bases, salts, and/or pressure. Additionally, the step of converting the mineralized gelatin solution to a mineralized gelatin may include refrigeration to facilitate the formation of a solid gel. According to certain embodiments, the DBM may be combined with the mineralized gelatin while the mineralized gelatin is in a solution or powder form.

Methods of the present invention may further include freeze-drying the DBM bone product. According to these embodiments, methods may further include re-hydrating the freeze-dried bone matrix product.

According to certain embodiments of methods for making a DBM bone product in accordance with the present invention, a DBM product may be created as depicted in FIG. 1. According to these embodiments, a single lot of donor bone is processed as depicted in the flow chart of FIG. 1. In particular, FIG. 1 depicts the splitting of a lot of freeze dried, ground cortical bone (2) for use in making DBM on the left of FIG. 1, and for use in preparing a mineralized gelatin carrier on the right of FIG. 1, which may be combined in accordance with the present invention in numerous different ways to form various DBM or bone grafting products.

The cortical bone lot (2) can be split by weight in a ratio depending on the gelatin yield. For example, the ratio of DBM bone to carrier bone can range from about 40:60 to about 95:5 by weight (i.e., the ratio of the weight of cortical bone used to produce DBM on the left of FIG. 1 to the weight of cortical bone used to produce a gelatin carrier on the right of FIG. 1). The ratio is a ratio of the original bone lot. According to certain embodiments, the split may be about 80:20 to about 95:5 or about 90:10. The actual ratio is dependent on the yield of gelatin from the mineralized gelatin process.

Using an example ratio of 90:10, 90% of the cortical bone lot (i.e., the first portion of the bone lot, which is being used to produce DBM) may be processed in a demineralization process (4) using standard demineralization techniques. For example, in step (4) ground cortical bone may be soaked in an acidic solution, such as 0.5 N hydrochloric acid (HCl) solution for a period of about 2-5 hours. This may be done for example, at around room temperature. By way of further example, in the demineralization process, the acid extraction may be done at a temperature that does not denature the collagen. This mineralized extract is then discarded, hence the term "demineralization". After the mineral is dissolved from the cortical bone, demineralized bone matrix particles remain. The DBM may then undergo a neutralization step (6) in which the DBM may be rinsed with water and/or saline and neutralized by buffering to bring the pH to 7. The wet DBM may then be subjected to a freeze-drying step (8) in which the wet DBM is freeze-dried into a dry, particulate form.

During the processing of the bone to form dried DBM, care should be taken to ensure that the biologically active growth factors maintain their activity. This may be done by minimizing the exposure of the bone and resultant DBM to high temperatures. It should be noted that the techniques depicted on the left of FIG. 1 may include any demineralization techniques known to those skilled in the art and are not limited to the specific technique set forth in FIG. 1 or to techniques discussed in this application.

The remaining 10% of the cortical bone lot (i.e., the second portion of the cortical bone lot, which is being used to produce a carrier, such as gelatin) may be processed to create the mineralized gelatin. In this process, gelatin is removed from the bone in an extraction process (10). The extraction process (10) may include exposing the second portion of the cortical bone lot to one or more of heat, acids, sonication, bases, salt, and/or pressure. For example, the bone may be placed in a more concentrated solution of acid than what is used in the processing of DBM, such as HCl, and heated to near boiling to dissolve the bone mineral and fully denature the collagen molecules into gelatin. In addition, sonication may be used to ultrasonically agitate the particles to accelerate the gelatin extraction process. In the gelatin extraction process, mineral is dissolved, but the higher temperature also denatures the collagen. In addition, in embodiments in which acid is used in the extraction process, an acid extraction solution (containing the mineral) is not removed and discarded. It becomes part of the gel.

The extraction process may include more than one extraction step. This produces a high quality mineralized gelatin solution, which may then be neutralized according to neutralizing step (12) and converted to a mineralized gelatin. According to the embodiments depicted in FIG. 1, the neutralized gelatin solution may undergo a freeze-drying step (14). The freeze-dried gelatin may be subjected to a reconstituting step (16) in which the gelatin is reconstituted with water or other solvent to form a gelatin solution with a specific concentration. Typically, the reconstituted gelatin solution is in the range of about 1-10% gelatin solution.

According to the embodiments depicted in FIG. 1, the mineralized gelatin solution may be subjected to a refrigeration step (18) in which the solution (either directly after neutralization step 12 or after the reconstituting step 16) is cooled to form a solid gel.

Specific techniques to accomplish the extraction, neutralization and/or conversion to mineralized gelatin may include, but are not limited to, methods in accordance with the present invention for making a mineralized carrier from cortical bone, discussed below. Variant methods may be employed however and remain within the scope of the present invention. For example, such methods may include forming a mineralized carrier from bone (rather than from DBM), and/or forming a mineralized carrier that includes calcium and phosphate. Additionally, the present invention includes forming a mineralized gelatin carrier by adding calcium and phosphate materials to a standard gelatin.

DBM and/or other bone graft materials can then be combined (20) with the gel to create a variety of bone graft products. Products resulting from the combination of the gel and the DBM in the examples depicted in FIG. 1 can be for example, in the form of a moldable putty, an extrudable gel, or a freeze dried sheet or block form, or any form in which the use of DBM may be advantageously used. By way of non-limiting example, the combination of DBM and gelatin may be processed in step 22 to form DBM putty.

The present invention is further directed to methods of forming a mineralized carrier from bone. The processing of bone may include extraction for example by exposure to one or more of heat, acids, sonication bases, salts, and/or pressure, to form an extracted gelatin solution; and neutralizing the extracted gelatin solution to form a neutralized solution. The processing may further include freeze-drying the neutralized solution to form a freeze-dried mineralized carrier. These steps are non-limiting and may include additional steps and/or may be in a different order than those specifically described herein and depicted in the Figures. For example, the extraction of mineralized gelatin from bone may be dependent on a number of factors. In the processes of the present invention, acid or base concentration, ratio of acid or base to bone, extraction temperature, extraction duration, sonication duration, and other variants can all affect the final quantity and quality of the mineralized gelatin. Those skilled in the art reading this disclosure would be able to fine tune the present methods in accordance with the desired product, to arrive at a desired quantity and quality of mineralized gelatin.

The methods of the present invention may further include performing one or more additional extractions to form one or more additional extracted gelatin solutions, and optionally combining the one or more of the extracted gelatin solutions before the neutralizing step. The methods may further include reconstituting the freeze-dried mineralized carrier with a liquid to form a liquid mineralized carrier. The methods may further include cooling the liquid mineralized carrier to about room temperature or below to form a solid or semi-solid mineralized carrier.

Figure 2:
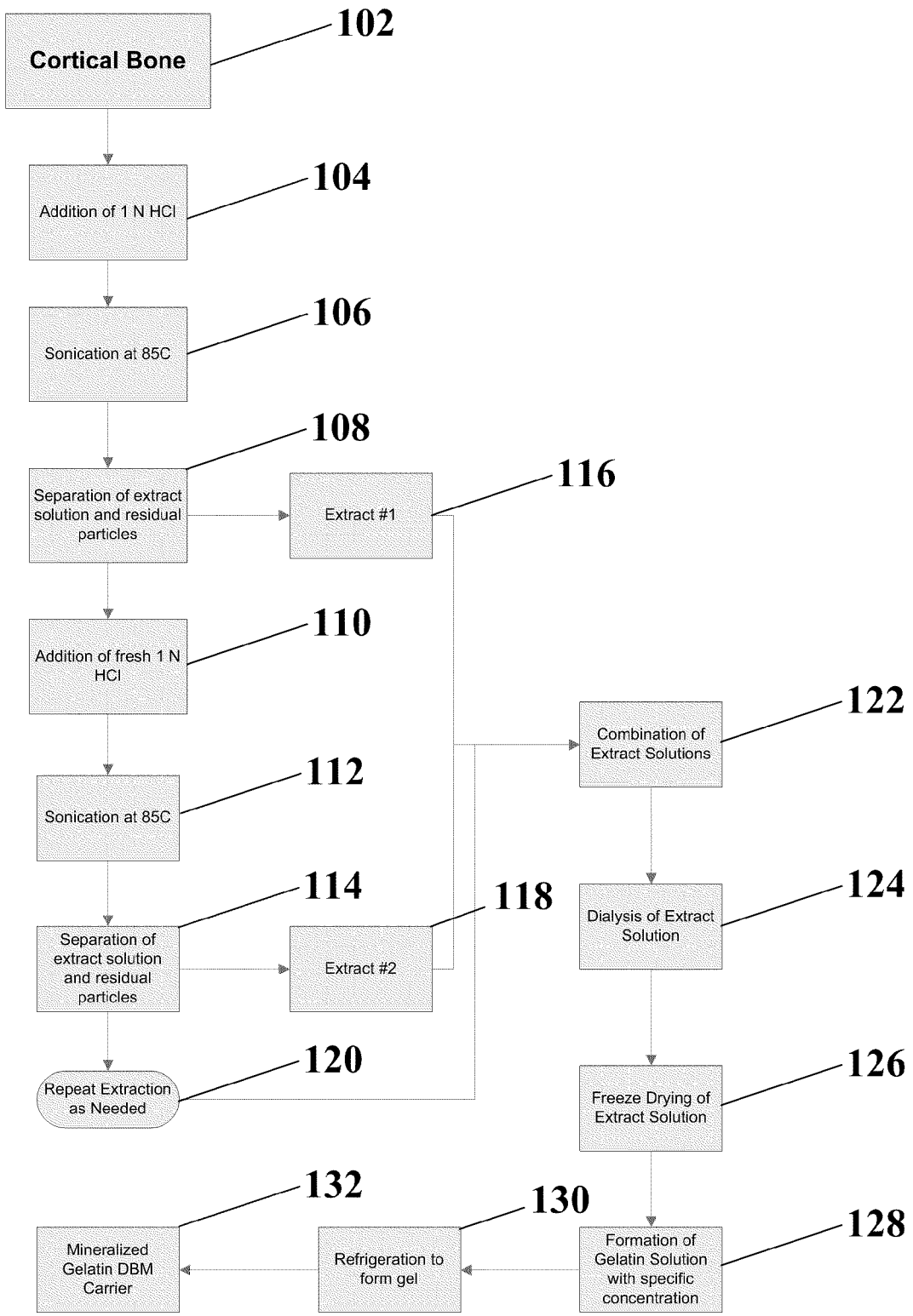
FIG. 2 is a flow chart of a detailed process for creating a mineralized gelatin carrier, in accordance with certain embodiments of the present invention. Mineralized carriers of the present invention may be used to carry DBM and/or other products such as autograft bone chips, allograft cortical bone chips, allograft cancellous bone chips, synthetic bone grafts, growth factors (BMP, TGF, VEGF, etc), cells (stem cells, marrow cell, osteoblasts), or any other material used in bone grafting.

FIG. 2 is a flow chart depicting non-limiting embodiments of methods of forming a mineralized carrier from bone in accordance with the present invention. According to the embodiments depicted in FIG. 2, cortical bone is exposed to acid, heat, and/or sonication to extract a gelatin solution from the bone, which may then be further processed to form a mineralized carrier. In the embodiments depicted in FIG. 2, according to a step (104) in the extracting process, cortical bone (102) is placed in an acid solution. The acid solution may include, but is not limited to, one or more acids such as hydrochloric acid, sulfuric acid, citric acid, acetic acid, and nitric acid. According to certain embodiments, such as that depicted in FIG. 2, hydrochloric acid is used. The concentration of the acid solution may range from about 0.5 M to about 10 M. According to certain embodiments, the concentration is about 1.0 M to about 3.0 M. The ratio of the bone to the acid may also affect the resulting gelatin quality. This may range from about 1 g in 1 ml of acid to about 1 g in 20 ml of acid. According to certain embodiments, the range is about 1:2.5 g/ml to about 1:5 g/ml.

In these embodiments, after the bone is placed in the acid solution, or acid is added to the bone, the bone is heated to dissolve the bone mineral and accelerate the breakdown of the collagen components of the bone into gelatin. According to certain embodiments, the acid may be heated prior to the bone addition. The heating may range from about 40° C. to about 100° C. to thermally degrade the collagen. According to certain embodiments, the range may be about 60° C. to about 85° C.

A sonication step (106) may be used to ultrasonically agitate the particles to accelerate the breakdown of collagen in the gelatin extraction process. Sonication of the bone, particularly while in acid at elevated temperatures can mechanically agitate the collagen into smaller fragments. Mechanical agitation such as stirring, homogenization, grinding, or milling can also be used to physically break apart the bone. In the example depicted in FIG. 2, sonication may be used constantly through the extraction process or at specific intervals. Additionally, the extraction time can also be modified to improve the effectiveness of the extraction step. For example, the extraction time can range from as short as 30 minute extraction cycles to 24 hour extraction cycles. According to certain embodiments, an approximately 2 to 4 hour extraction cycle is used.

After a set period of time, a separation step (108) is performed in which a first extract or extraction solution (116) may be removed. The separation is performed for example, by decanting, filtering, or centrifugation extraction techniques. As long as the wet residual is separated from the solution, it does matter which technique is used. The residual remaining after removal of the first extract may then be further processed by steps that include the addition (110) of fresh acid to the residual), a sonication step (112) and a separation step (114) to remove a second extract or extraction solution (118) from the processed residual. Further extraction steps (120) may be performed to any remaining residual as desired or until the bone is essentially fully solubilized.

After the extraction process is complete, the extraction solutions (116 and 118) can be combined (122) into a single solution. A neutralization step (124) may then be performed using techniques such as, but not limited to, buffering, dialysis, and ultrafiltration to form a gelatin solution. According to certain embodiments, calcium hydroxide base may be used in the neutralization. According to other embodiments, dialysis tubes with a molecular weight cutoff of 10,000-15,000 Da may be used. Alternatively, each extraction solution may be separately neutralized soon after extraction. The extracts may optionally be frozen (independently or combined) before neutralization to prevent further breakdown of gelatin fragments.

Figure 3:
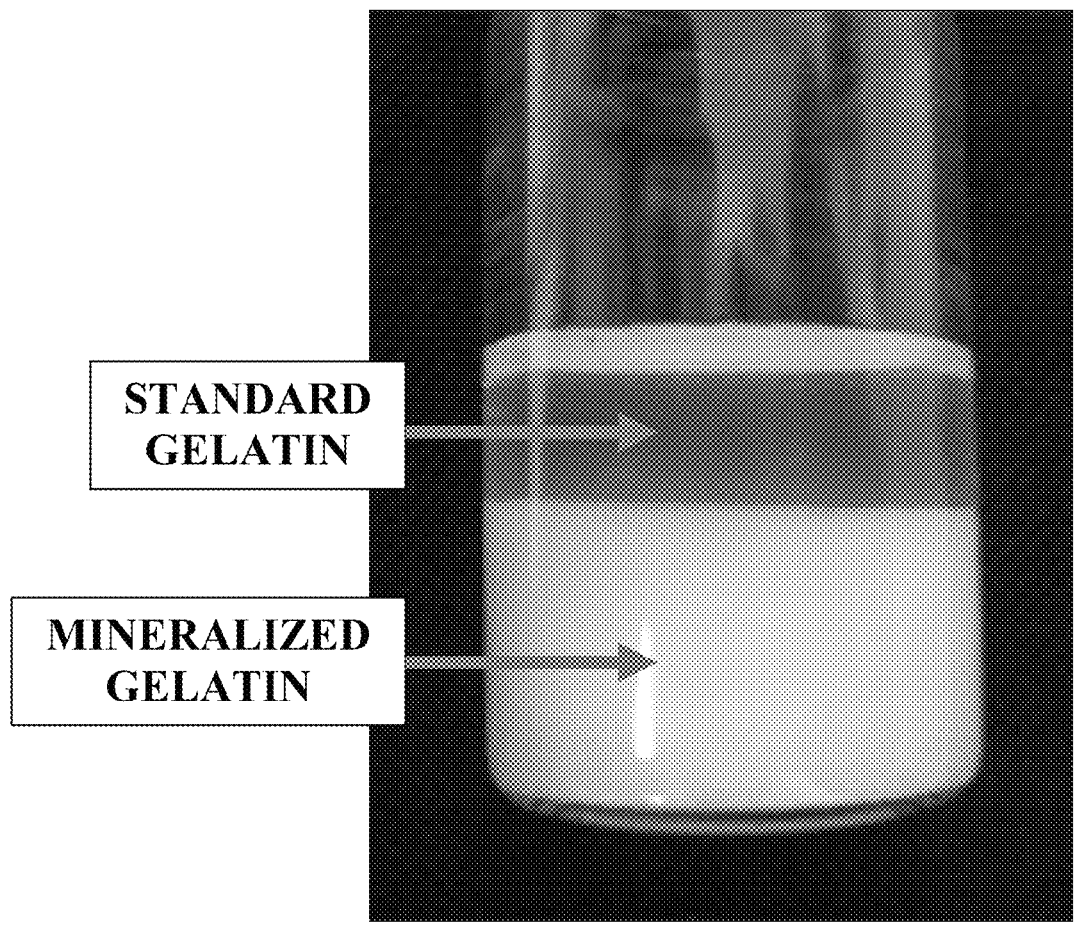
FIG. 3 is a photograph of a gel of both standard and mineralized gelatin.

Depending on the concentration of the resultant neutralized gelatin solution, the carrier may gel when cooled to a temperature of between about 32 and 50° F., or about 2 to 10° C. FIG. 3 shows that the gelatin obtained by the present methods is visibly different than normal DBM derived gelatin. As depicted in FIG. 3, there is a clear distinction between mineralized gelatin and normal gelatin. A standardized or specific gelatin concentration may be obtained by performing a freeze-drying step (126) to freeze-dry the mineralized gelatin solution to essentially isolate the mineralized gel. Once the mineralized gel is freeze-dried, a reconstituting (rehydrating) step (128) may be performed in which the dry mineralized gel can be reconstituted (rehydrated) with water or other solvent in a specific concentration to create a standardized gelatin solution. The standardized solution may then be cooled in a refrigeration step (130) to form a gel. The concentration of the gelatin in water can be used to modify the properties of the resulting gels. Higher gelatin concentrations can be used for example, to create stronger gels. According to certain embodiments, a gelatin concentration of about 2-10% g/ml can be used to create a gel carrier for DBM particles. The gel may then be further processed (132) to form various mineralized carriers, such as DBM carriers.

The mineralized gelatin carrier may be stored, sold, or used in a variety of forms, including, but not limited to an unconstituted freeze-dried form resulting for example after step 126, in a reconstituted liquid form resulting for example after 128, in a refrigerated gel form resulting for example after step 18, or as a mineralized gelatin DBM carrier resulting for example after step 22.

The mineralized gelatin carrier may be used to fabricate a variety of DBM products. For example, a DBM putty can be created by mixing dry DBM particles into the mineralized gel. According to certain embodiments, the DBM concentration in the gel may be about 30-35% by weight. A putty capable of being extruded through a syringe (often called a DBM gel or paste) can be created by lowering the DBM content and increasing the gelatin content. According to certain embodiments, extrudable DBM putties can be formed using about 25-30% DBM concentration by weight.

DBM sheets and blocks can also be formed from the mineralized gelatin/DBM mixture. In this form, a DBM product, such as DBM putty or gel, may be molded into a desired shape and then freeze-dried to remove the water component. The result is a DBM sponge capable of absorbing additional fluid. These sponges are designed to be rehydrated for example, by a surgeon inserting the bone product, with a liquid including, but not limited to, sterile water, sterile saline, blood, platelet rich plasma, growth factor solutions, marrow aspirate, and/or cellular suspensions (mesenchymal stem cells, osteoblasts, etc).

The present invention further provides mineralized carriers in various forms including in a freeze-dried powder form, a reconstituted liquid form, and mineralized carriers capable of being formed into or actually formed into a solid or semi-solid mineralized carrier, such as putties, gels, blocks, sheets, sponges, or any other form contemplated by those skilled in the art. Accordingly, methods of the present invention may further include one or more steps to achieve the desired form and/or shape. For example, the methods may include the step of forming the liquid mineralized carrier into a solid or semi-solid mineralized carrier selected from the group consisting of a sheet, putty, paste, block, and gel, and may optionally further include shaping the liquid mineralized carrier to form a shaped solid or semi-solid mineralized carrier.

Mineralized carriers in accordance with the present invention may be carriers formed by the present methods or may be formed by modified methods, including other methods, which like the present methods, include the mineralized carrier being made directly from bone rather than from DBM, and/or result in mineralized carrier that include calcium and phosphate ions, such as calcium and phosphate salts. Accordingly, the present invention also provides mineralized carriers that include gelatin and calcium and phosphate.

Mineralized carriers in accordance with the present invention may include the component being carried, such as DBM, and/or one or more additional components such as other biologically active ingredients, and/or thickening materials. Accordingly, the present invention further provides bone products that include DBM and a mineralized carrier, such as the carriers produced by the methods disclosed herein. The DBM and the mineralized carrier may be integrally mixed in the bone product or in discrete portions of the bone product depending for example on the intended use of the product.

The one or more additional components that may be added to the mineralized carriers or bone products of the present invention may include any components that may be advantageous to bone grafting, as would be apparent to those skilled in the art. For example, it may be advantageous to add one or more biologically active ingredients to the mineralized carrier of the present invention, which may or may not be related to the connective tissue repair capabilities of the composition. Suitable active ingredients include DBM and the insoluble extraction product containing residual, bone morphogenetic proteins and related proteins such as cartilage derived morphogenetic proteins (CDMPs). Other active ingredients that may be added to the composition, including bone-derived materials such as cortical or cancellous bone chips and bone mineral, osteogenic chemicals (e.g., L-arginine), osteogenic peptides (e.g., OSA), osteogenic growth factors (e.g., transforming growth factor-beta [TGF-β], insulin-like growth factor [IGF], platelet derived growth factor [PDGF], vascular endothelial growth factor [VEGF], fibroblast growth factor [FGF]), and recombinant BMPs (e.g., rBMP-2, rBMP-7), fibronectin, and blood-derived proteins. When added in appropriate combinations, these active ingredients may assist bone repair, cartilage repair, ligament and tendon repair, meniscal repair, and other musculoskeletal applications.

The product to be delivered, such as DBM, may be added to the mineralized carrier at any of several steps in the process of making the mineralized carrier, depending on the result to be achieved. For example, if it is desired that the DBM be integrally mixed with the mineralized carrier in a final product, the DBM may be added to the mineralized carrier in its freeze-dried or liquid form, before the carrier is made into its final form and shape. The DBM may alternatively be added to the mineralized carrier in its solid or semi-solid form, for example where it is desired that the DBM and mineralized carrier may form discrete portions of the final product, such as discrete portions of a block. In addition, the mineralized gelatin may be used as a carrier for non-DBM containing bone graft materials. The gelatin may be used as a carrier for materials such as autograft, allograft cortical chips, allograft cancellous chips, synthetic bone graft particles, growth factors (such as BMP, TGF-B, VEGF, FGF), and/or cells (marrow cells, stem cells, bone cells, cartilage cells).

As indicated above, DBM products in accordance with the present invention, including for example, putty and gel, can be optionally mixed with other graft materials such as bone chips (including for example cortical and cancellous bone chips), synthetic graft granules, and autograft tissue. Other components may be added for example, to assist with making the form of the carrier or bone product, such as components that affect the viscosity, hardness, shape and other physical characteristics of the carrier or bone product. For example, one or more thickening agents may be added to the carrier or DBM bone products of the present invention. Components may be added at various stages of the process of making the mineralized carrier or bone products, or after formation of a bone product, such as to the surface of the bone product.

The one or more thickening materials in accordance with the present invention may be an active ingredient or biologically inert. Suitable thickening materials include for example, collagen, bone mineral, an insoluble extraction product from the present methods, hydroxyapatite, tricalcium phosphate, biphasic calcium phosphate, calcium sulfate, calcium carbonate, biological glasses, and natural or synthetic polymers. DBM, and/or a reverse phase medium may be used as a thickening material with or without added proteins. The reverse phase medium may be an aqueous mixture of Pluronic F127 (BASF Corp.) in an amount sufficient to confer a reverse phase property to the composition, such as approximately 20-40% w/w, or about 23-32% w/w, or about 25% w/w or about 35% w/w mixture of Pluronic® F127 and water. Other reverse phase media include aqueous mixtures of derivatives of Pluronic® F127.

The biological, physicochemical and biodegradation properties of the composition may be altered by known cross-linking agents such as chemicals (e.g., glutaraldehyde or formaldehyde) or radiation (e.g. gamma or electron beam). For example, electron beam (E-beam) radiation may be used to irradiate the wet or dry materials at doses between about 5 and about 50 kGray.

Resulting products or compositions of the present invention may be used in several different manners. DBM products in accordance with the present invention can be prepared for, for example, injection or insertion at, into, onto, or near bone or chondral defect sites, cartilage repair sites, or other musculoskeletal sites. The manner of injection or insertion is not essential, but may be for example via syringe in the case of injection and insertion may be by creating a surgical opening to access the bone or chondral defect site.

According to certain embodiments, a composition including the carriers or products of the present invention may be applied to lyophilized, cancellous bone chips; or bone chips may be dipped into the composition. The bone chips, coated with the composition, may be dried. The drying step may be conducted by any conventional drying process, including lyophilization or oven drying. The coated bone chips may be used as or in surgical implants at, in, on, or near bone defect sites, cartilage repair sites, or other musculoskeletal sites. Alternatively, the coating may be applied to larger segments of bone, artificial implants, or any other kind of surgical implant.

Alternatively, the dry soluble extraction product or concentrate may be mixed with aqueous alcohol or other volatile solutions, cast into a desired shape and dried to form a sponge-like material. For example, one to six carbon alcohol, such as ethanol, may be used. Moreover, 1 to 20 percent alcohol by volume solution may be used. The resulting composition may be cast into a sheet or other shape with or without other added materials. The sheet or other shape is dried. Drying may be done by any conventional method, including lyophilization or air-drying. Preferably, drying is by lyophilization.

In certain embodiments, the sheet or shape formed with an alcohol solution as described above may be used as or as part of a surgical implant. Where a sheet is used, it may be used as a wrap around an area or as a patch inserted into a bone defect site, e.g., insertion into a bone defect, a chondral defect, a spinal fusion cage or a pre-reamed acetabular bed.

Products in accordance with the present invention can also be used as a coating on surgical implants or devices to be inserted at, into, onto or near bone defect sites, cartilage repair sites, or other musculoskeletal sites. Accordingly, the present invention further encompasses surgical implants or devices comprising a surgical implant coated with a mineralized carrier and/or a bone product or composition, which includes a mineralized carrier in accordance with the present invention.

The present invention is further directed to kits that include a mineralized carrier in accordance with the present invention. The mineralized carrier may be in powder, liquid, solid or semi-solid form, for example in the form of a gel, putty, paste, sheet, block, sponge or other form. Accordingly, the mineralized carrier may be included in the kit independent from the item to be carried, or may be in the kit in a final, bone product form, or as a coating or component of a surgical implant or device included in the kit. In kits where the mineralized carrier is included independently from the component to be carried, the kit may further include the component to be carried (such as DBM). Such kits including the carrier and component to be carried separately would allow a user to determine which ratio of e.g., DBM to carrier they wish to use.

Kits in accordance with the present invention may include one or more of the following: a liquid for reconstituting mineralized carrier from a powder form; a liquid to be added to a bone product in a sponge form; a container for combining the carrier with one or more other components; and/or an apparatus (such as a form or mold) in which or on which to form a carrier into a specific shape. Kits may further include any other components to be combined with or added to the carrier. Furthermore, kits in accordance with the present invention may include one or more tools or other components to assist in inserting a bone product, surgical implant or device into a patient.

The present invention further includes methods of treating a patient, which include providing a patient in need of treatment, such as a patient with a bone defect, with a bone product and/or an implant that includes a bone product (for example coated on the implant), in accordance with the present invention.

The following examples illustrate specific embodiments of the invention. The examples set forth herein are meant to be illustrative and should not in any way serve to limit the scope of the claimed invention. As would be apparent to skilled artisans, various changes and modifications are possible and are contemplated within the scope of the invention described, and may be made by persons skilled in the art without departure from the spirit of the invention.

EXAMPLES

Example 1

This example details an extraction process according to certain methods of forming a mineralized carrier in accordance with the present invention. Cortical bone is heated in an oven at about 85° C. for about 1 hour, and sonicated at about 60° C. for about 1 hour. This is repeated once for a total extraction time of about 4 hours. At this point, the extraction solution is isolated from the residual bone through techniques such as decanting, or filtration, resulting in a first extract. This first extract can be frozen to prevent further breakdown of the gelatin fragments or can be immediately neutralized using buffering, dialysis, ultrafiltration, or other neutralization techniques.

The residual bone is then put through additional extraction steps with fresh acid until the collagen is completely dissolved. The subsequent extraction steps may be conducted using modified extraction conditions to fully dissolve the remaining collagen. The second extraction included exposing the residual bone to fresh 1 N HCl in an oven for about 1 hour followed by sonication at about 60° C. for about 1 hour, resulting in a second extract. The second extract can be frozen to prevent further breakdown of the gelatin fragments, can be combined with the first extract before neutralization, or can be immediately neutralized using buffering, dialysis, ultrafiltration, or other neutralization techniques. The extract can then be freeze dried to allow for future reconstitution.

Example 2

The freeze dried mineralized gelatin from Example 1 can then be combined with sterile water to produce a 5% gelatin solution. Once fully dissolved, the gelatin solution is placed in a refrigerator at 4° C. to cause the material to gel. At this point, a mixture of 30% DBM and 70% gelatin (by weight) can be formed to create a moldable DBM putty. Once thoroughly mixed, the DBM putty is stable at room temperature.

Although this invention has been described in certain specific embodiments, many additional modifications and variations would be apparent to those skilled in the art. For example, many modifications may be made by those skilled in the art to the process conditions, such as temperature, amount and type of acid, base and, or salt used, amount of sonication, number of extraction repetitions, and the like to achieve a desired product. It is therefore to be understood that this invention may be practiced other than as specifically described. Thus, the present embodiments of the invention should be considered in all respects as illustrative and not restrictive.

What is claimed is:

1. A bone product comprising a mineralized carrier comprising bone gelatin solubilized and extracted from bone while retaining solubilized minerals from the bone, and the retained solubilized minerals from the bone;
   wherein the bone product further comprises bone graft materials.

2. A bone product comprising a mineralized carrier produced by a method comprising
   solubilizing and extracting gelatin solution from bone, while retaining solubilized minerals from said bone in said gelatin solution;
   neutralizing the pH of the solubilized and extracted gelatin solution to form a neutralized mineralized carrier solution; and
   processing the neutralized mineralized carrier solution into a mineralized carrier comprising bone gelatin and the solubilized minerals from bone,
   wherein the bone product further comprises bone graft materials.

3. The bone product of claim 2, wherein said mineralized carrier is a freeze dried mineralized carrier.

4. The bone product of claim 2, wherein said mineralized carrier is a liquid mineralized carrier formed by reconstituting a freeze-dried mineralized carrier.

5. The bone product of claim 2, wherein said mineralized carrier is a solid or semi-solid mineralized carrier formed by cooling a liquid mineralized carrier that was reconstituted from a freeze-dried mineralized carrier.

* * * * *